United States Patent
Balzer et al.

(10) Patent No.: US 7,962,218 B2
(45) Date of Patent: Jun. 14, 2011

(54) SYSTEM AND METHOD FOR TREATING PARKINSON'S DISEASE AND OTHER MOVEMENT DISORDERS

(75) Inventors: Jeffrey Balzer, Allison Park, PA (US); Allen Wyler, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 675 days.

(21) Appl. No.: 11/867,654

(22) Filed: Oct. 4, 2007

(65) Prior Publication Data

US 2008/0195175 A1    Aug. 14, 2008

Related U.S. Application Data

(63) Continuation of application No. 10/731,731, filed on Dec. 9, 2003, now Pat. No. 7,299,096, which is a continuation-in-part of application No. 09/802,808, filed on Mar. 8, 2001, now Pat. No. 7,010,351.

(60) Provisional application No. 60/432,073, filed on Dec. 9, 2002.

(51) Int. Cl.
*A61N 1/00* (2006.01)

(52) U.S. Cl. .......................................................... 607/45
(58) Field of Classification Search ..................... 607/45
See application file for complete search history.

(56) References Cited

U.S. PATENT DOCUMENTS

| 5,769,861 | A | * | 6/1998 | Vilsmeier | 606/130 |
| 6,144,875 | A | * | 11/2000 | Schweikard et al. | 600/427 |
| 2005/0228291 | A1 | * | 10/2005 | Chance | 600/476 |
| 2006/0241717 | A1 | * | 10/2006 | Whitehurst et al. | 607/45 |

* cited by examiner

*Primary Examiner* — Scott M Getzow
(74) *Attorney, Agent, or Firm* — Melissa Acosta; Christopher S. L. Crawford; Peter Lando

(57) ABSTRACT

Systems and methods for treating movement disorders using cortical stimulation. In one embodiment, a method for treating movement disorders comprises determining a site at the cortex of the brain of a patient related to a movement disorder of an afflicted body part. The site can be determined by obtaining a representation of neural activity occurring in the cortex of the patient and correlating an area of neural activity with the afflicted body part. The method can also include applying neural stimulation, such as electrical or magnetic waveforms, directly to the site.

16 Claims, 9 Drawing Sheets

2

SYSTEM AND METHOD FOR TREATING PARKINSON'S DISEASE AND OTHER MOVEMENT DISORDERS

CROSS-REFERENCE TO RELATED APPLICATIONS

The present application is a continuation-in-part of U.S. application Ser. No. 09/802,808 filed on Mar. 8, 2001, and claims the benefit of U.S. Provisional Application No. 60/432,073, both of which are herein incorporated by reference.

TECHNICAL FIELD

The present invention is directed toward systems and methods for treating movement disorders, such as Parkinson's Disease, that are associated with abnormal neural activity in the brain.

BACKGROUND

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex, the basal ganglia, the thalamus, and the motor cortex cooperatively interact to facilitate motor function control.

Many problems or abnormalities with body functions can be caused by damage, disease, and/or disorders in the brain. For example, Parkinson's Disease (PD) is related to the degeneration or death of dopamine producing neurons in the substantia nigra region of the basal ganglia in the brain. Dopamine is a neurotransmitter that transmits signals between areas of the brain. As the neurons in the substantia nigra deteriorate, the reduction in dopamine causes abnormal neural activity that results in a chronic, progressive deterioration of motor function control. Conservative estimates indicate that PD may affect more than one million individuals in the United States alone.

PD patients typically exhibit one or more of four primary symptoms. One primary symptom is a tremor in an extremity (e.g., a hand) that occurs while the extremity is at rest. Other primary symptoms include a generalized slowness of movement (bradykinesia); increased muscle rigidity or stiffness (rigidity); and gait or balance problems (postural dysfunction). In addition to or in lieu of these primary symptoms, PD patients may exhibit secondary symptoms including: difficulty initiating or resuming movements; loss of fine motor skills; lack of arm swing on the affected side of the body while walking; foot drag on the affected side of the body; decreased facial expression; voice and/or speech changes; cognitive disorders; feelings of depression or anxiety; and/or other symptoms.

Effectively treating PD or other movement disorders related to neurological conditions can be very difficult. Current treatments for PD symptoms include drugs, ablative surgical intervention, and/or neural stimulation. Drug treatments or therapies may involve, for example, the administration of a dopamine precursor that is converted to dopamine within the central nervous system (i.e., Levodopa (L-dopa)). Other types of drug therapies are also available. Unfortunately, drug therapies frequently become less effective or ineffective over time for an undesirably large patient population. A PD patient may require multiple drugs in combination to extend the time period of efficacy of drug therapies. Drug treatments additionally have a significant likelihood of inducing undesirable physical side effects; motor function complications such as uncontrollable involuntary movements (dyskinesias) are a particularly common side effect. Furthermore, drug treatments may induce undesirable cognitive side effects such as confusion and/or hallucinations.

Ablative surgical intervention for PD typically involves the destruction of one or more neural structures within the basal ganglia or thalamus that have become overactive because of the lack of dopamine. Unfortunately, such neural structures reside deep within the brain, and hence ablative surgical intervention is a very time consuming and highly invasive procedure. Potential complications associated with the procedure include risk of hemorrhage, stroke, and/or paralysis. Moreover, because PD is a progressive disease, multiple deep brain surgeries may be required as symptoms progressively worsen over time. Although ablative surgical intervention may improve a PD patient's motor function, it is not likely to completely restore normal motor function. Furthermore, since ablative surgical intervention permanently destroys neural tissue, the effects of such intervention cannot be readily adjusted or "fine tuned" over time.

Neural stimulation treatments have shown promising results for reducing some of the symptoms associated with PD. Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials in the event that the integration exceeds a threshold potential. A neural firing threshold, for example, may be approximately −55 mV. Action potentials propagate to the neuron's synapses and are then conveyed to other synaptically connected neurons.

Neural activity in the brain can be influenced by neural stimulation, which involves the application of electrical and/or magnetic stimuli to one or more target neural populations within a patient using a waveform generator or other type of device. Various neural functions can thus be promoted or disrupted by applying an electrical current to one or more regions of the brain. As a result, researchers have attempted to treat certain neurological conditions, including PD, using electrical or magnetic stimulation signals to control or affect brain functions.

Deep Brain Stimulation (DBS) is a stimulation therapy that has been used as an alternative to drug treatments and ablative surgical therapies. In DBS, one or more electrodes are surgically implanted into the brain proximate to deep brain or subcortical neural structures. For treating PD or other movement disorders, the electrodes are positioned in or proximate to the ventrointermediate nucleus of the thalamus; basal ganglia structures such as the globus pallidus internalis (GPi); or the Subthalamic Nucleus (STN). The location of the stimulation site for the electrodes depends upon the symptoms that a patient exhibits and the severity of the symptoms.

In a typical DBS system, a pulse generator delivers a continuous or essentially continuous electrical stimulation signal having a pulse repetition frequency of approximately 100 Hz to each of two deep brain electrodes. The electrodes are may be positioned bilaterally on the left and right sides of the brain relative to particular neural structures such as those indicated above. U.S. Pat. No. 5,883,709 discloses one conventional DBS system for treating movement disorders.

Although DBS therapies may significantly reduce one or more PD symptoms, particularly when combined with drug treatments, they are highly invasive procedures. In general, configuring a DBS system to properly function within a patient requires two time consuming, highly invasive surgical procedures for implanting the DBS electrodes. Each such surgical procedure has essentially the same risks as those described above for ablative surgical intervention. Moreover, DBS may not provide relief from some movement disorders.

Motor Cortex Stimulation (MCS) is another type of brain stimulation treatment that has been proposed for treating Parkinson's Disease. MCS involves the application of stimulation signals to the motor cortex of a patient. One MCS system includes a pulse generator connected to a strip electrode that is surgically implanted over a portion of only the motor cortex (precentral gyrus). The use of MCS to treat PD symptoms is described in Canavero, Sergio, *Extradural Motor Cortex Stimulation for Advanced Parkinson's Disease: Case Report*, Movement Disorders (Vol. 15, No. 1, 2000).

Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating PD symptoms. Present MCS techniques, however, fail to address or adequately consider a variety of factors that may enhance or optimize the extent to which a patient experiences short term and/or long term relief from PD symptoms.

DETAILED DESCRIPTION

The following disclosure describes several embodiments and systems for treating PD and other movement disorders using cortical stimulation. Several embodiments and features of methods and systems for treating PD in accordance with the invention are set forth and described in FIGS. 1-6. Additional embodiments and features of methods and systems for treating movement disorders, including PD, are set forth and described in FIGS. 7-9. It will be appreciated that other embodiments in accordance with the invention can include additional procedures or different features than those shown in FIGS. 1-9. Additionally, several embodiments of methods and systems in accordance with the invention may not include all of the features shown in these figures. Additionally, like reference numbers refer to similar or identical components or procedures throughout the figures.

A. Embodiments for Treating PD

Figure 1:
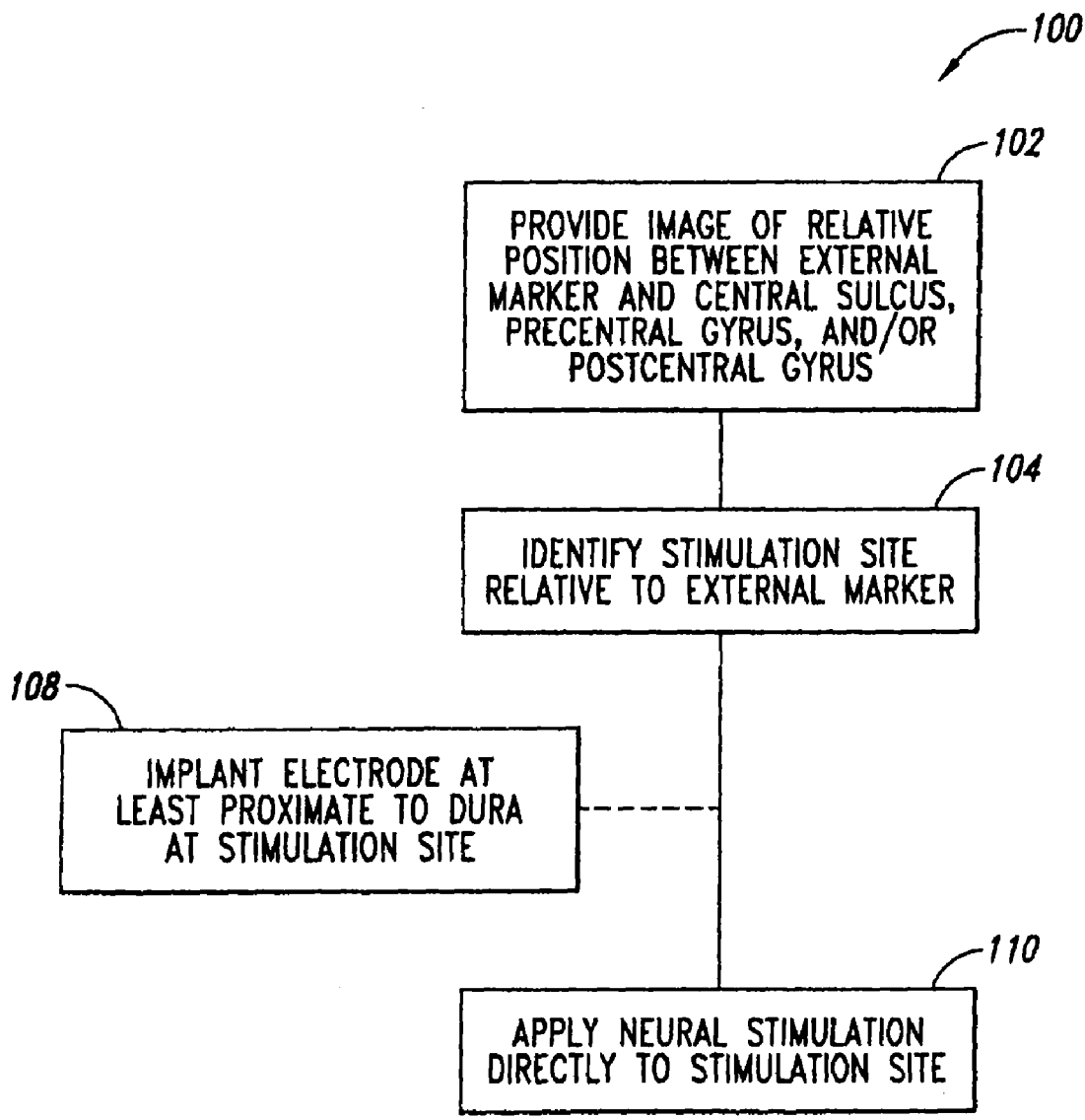
FIG. 1 is a flow chart illustrating methods for treating movement disorders in accordance with several embodiments of the invention.

FIG. 1 is a flow chart illustrating several methods for treating movement disorders in accordance with embodiments of the invention. The methods shown in FIG. 1 are particularly useful for treating PD. In one embodiment, a method 100 for treating movement disorders includes an imaging procedure 102 in which an image of the relative position between external markers and at least one of the central sulcus, precentral gyrus, and/or the postcentral gyrus of a patient is provided. The external markers can be anatomical features of the patient or fiducials that are attached to the patient. For example, the external markers can be fiducials that are attached to the skull of the patient. The method 100 also includes a site selection procedure 104 that involves identifying a stimulation site relative to the external markers using the images obtained in the imaging procedure 102. The stimulation site is generally proximate to the dura of the patient and over at least the precentral gyrus of the cortex. As explained in more detail below, the stimulation site can also be located over the central sulcus and/or the postcentral gyrus of the patient. The imaging procedure 102 and the site selection procedure 104 result in an accurate determination of the location of the underlying cortical features relative to external landmarks on the patient. As explained in more detail below, this is expected to significantly improve the efficacy of stimulation therapies for treating PD and other movement disorders.

The method 100 can further include a stimulating procedure 110 in which neural stimulation is applied directly to the stimulation site. The neural stimulation can be an electrical current applied epiduraly or subduraly to the stimulation site. When the neural stimulation is an electrical current applied directly to the cerebral cortex proximate to the dura, the method 100 includes an implanting procedure 108 in which an electrode is implanted at least proximate to the dura at the stimulation site. The implanting procedure 108 accordingly occurs after the site selection procedure 104 and before the stimulating procedure 110. In other embodiments, the neural stimulation of the stimulating procedure 110 can be transcutaneous magnetic stimulation. Several aspects of each of the procedures 102-110 are described in more detail below with respect to FIGS. 2A-5.

Figure 2A:
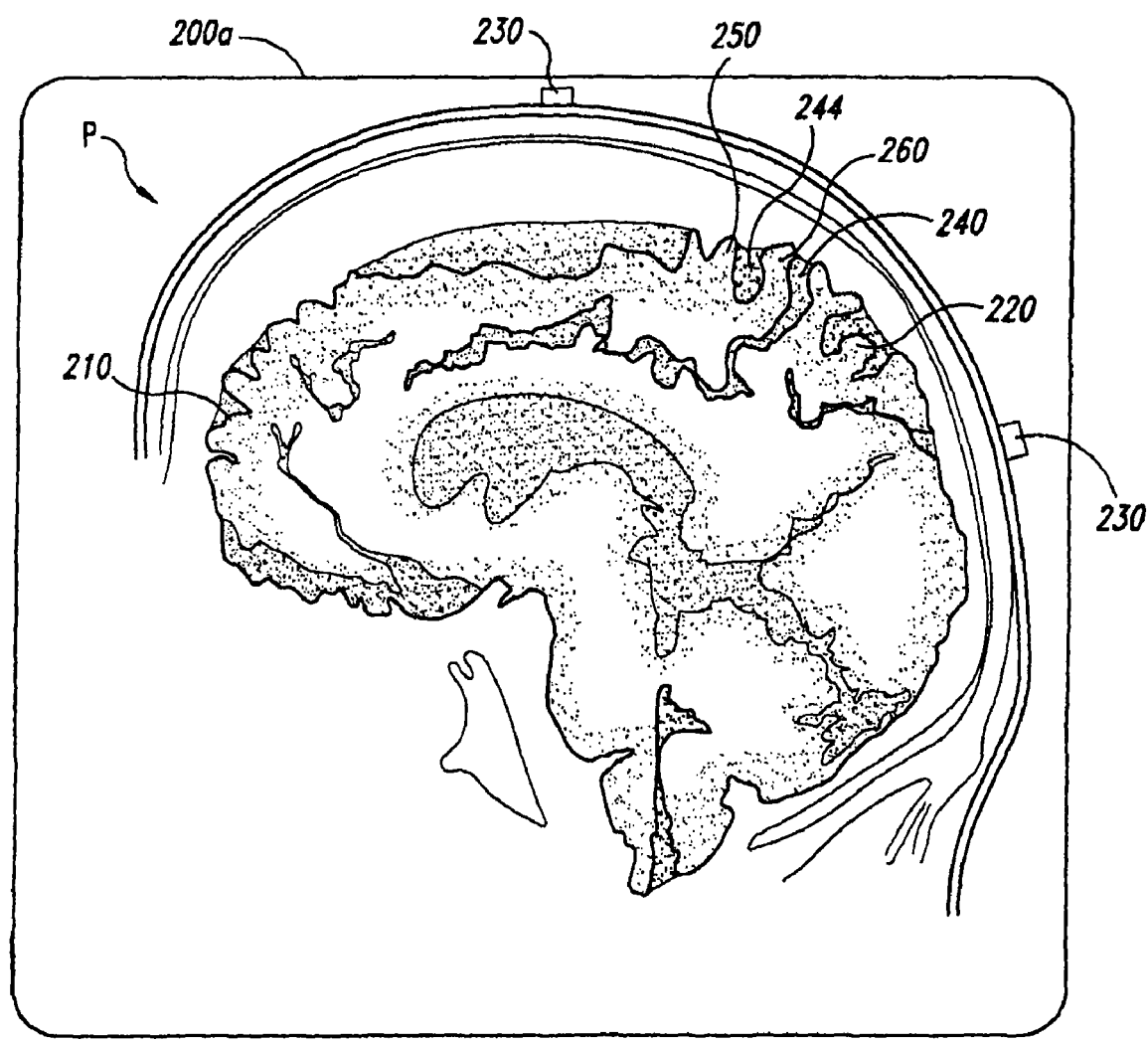
FIG. 2A is an image showing a mid saggital section of a brain of a patient.
Figure 2B:
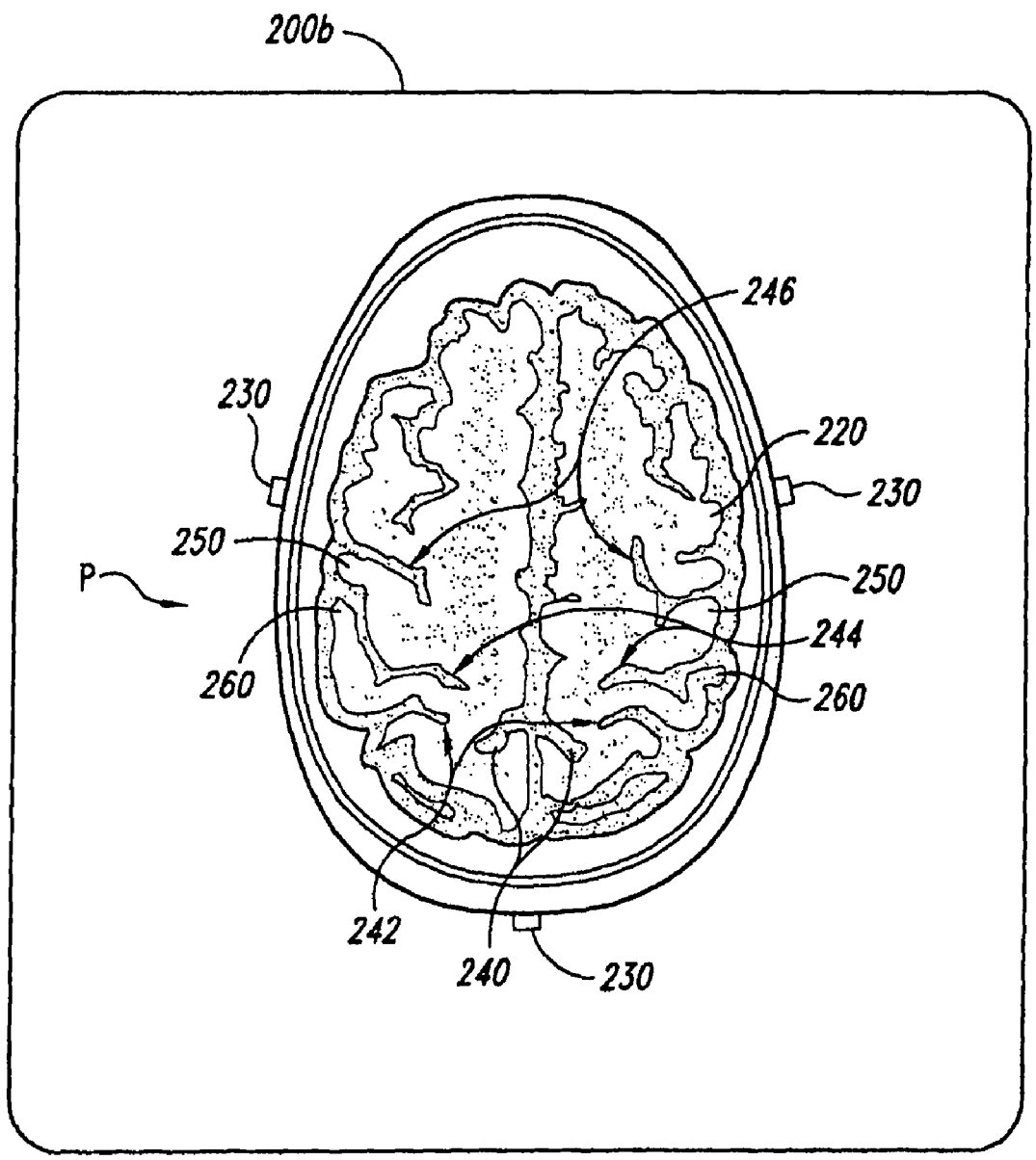
FIG. 2B is an image showing an axial view of a portion of the cerebral cortex of the brain of the patient.

FIGS. 2A and 2B are examples of images provided by the imaging procedure 102 (FIG. 1) for use in the site selection procedure 104 (FIG. 1). The imaging procedure 102 can be Magnetic Resonance Imaging (MRI), CT imaging, fMRI imaging or other suitable processes. FIG. 2A is a magnetic resonance image 200a showing the brain 210 of a patient P along a mid saggital section. The image 200a shows the location of various features of the cerebral cortex 220 relative to fiducial markers 230 attached to the skull of the patient P.

One embodiment of the site selection procedure 104 involves locating the pars marginalis sulcus 240 of the cortex 220 using the image 200a of the mid saggital section. This particular image is useful because the pars marginalis sulcus is the only sulcus that can be followed into the interhemispheric fissure in this view. Based on the location of the pars marginalis sulcus shown in image 200a, this position can be extrapolated to an axial image to determine the location of the central sulcus, the postcentral gyrus, and the precentral gyrus on the cortex 220 relative to the external markers.

The site selection procedure 104 (FIG. 1) continues with an axial image of the cortex 220. FIG. 2B is a magnetic resonance image 200b of a brain taken along an axial section. Referring to FIG. 2B, the pars marginalis sulcus 240 appears as a small, symmetrical sulcus extending bilaterally out from the interhemispheric fissure. Based upon the position of the pars marginalis sulcus 240, the position of the postcentral sulcus 242 can be determined by moving laterally (i.e., outward) from the pars marginalis sulcus 240. The postcentral sulcus 242 forms the posterior boundary of the postcentral gyrus 260, and thus the central sulcus 244 can be identified as the anterior boundary of the postcentral gyrus 260. Similarly, the central sulcus 244 forms the posterior boundary of the precentral gyrus 250 and the precentral sulcus 246 forms the anterior boundary of the precentral gyrus 250.

The site selection procedure 104 can also involve identifying an external region on the patient relative to the location of the central sulcus 244. After identifying the location of the central sulcus 244 on the image 200b, the location of the central sulcus 244 is noted relative to the external markers 230. Using standard neuronavigational MRI techniques, the data from the images can be transferred into an intraoperative navigational station that locates the external position on the scalp of the patient overlying the central sulcus 244 relative to the position of the fiducial markers 230. The external position accordingly defines the general area where stimulation will be applied. The actual stimulation site is generally under the scalp at an area that is proximate to the dura of the patient and aligned with the external position identified on the patient.

Figure 3A:
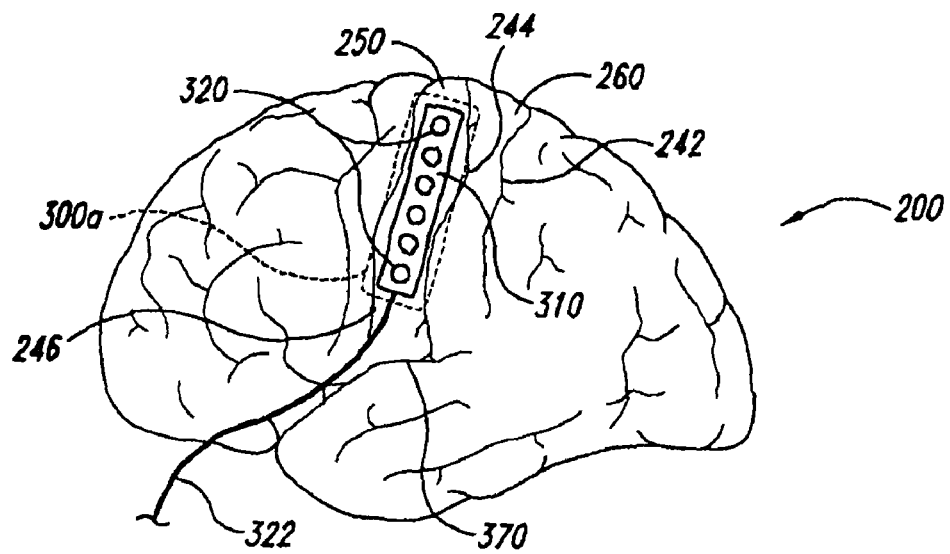
FIG. 3A is a side view of a brain of a patient with an electrode array implanted in accordance with one embodiment of the invention.
Figure 3B:
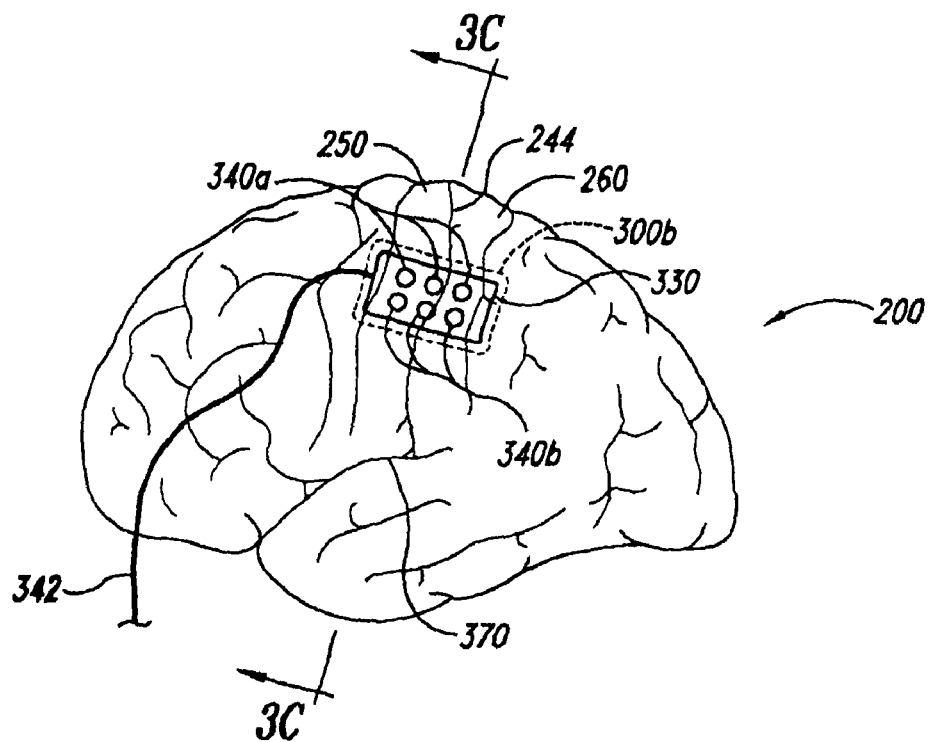
FIG. 3B is a side view of a brain of a patient with an electrode array implanted in accordance with another embodiment of the invention.
Figure 3C:
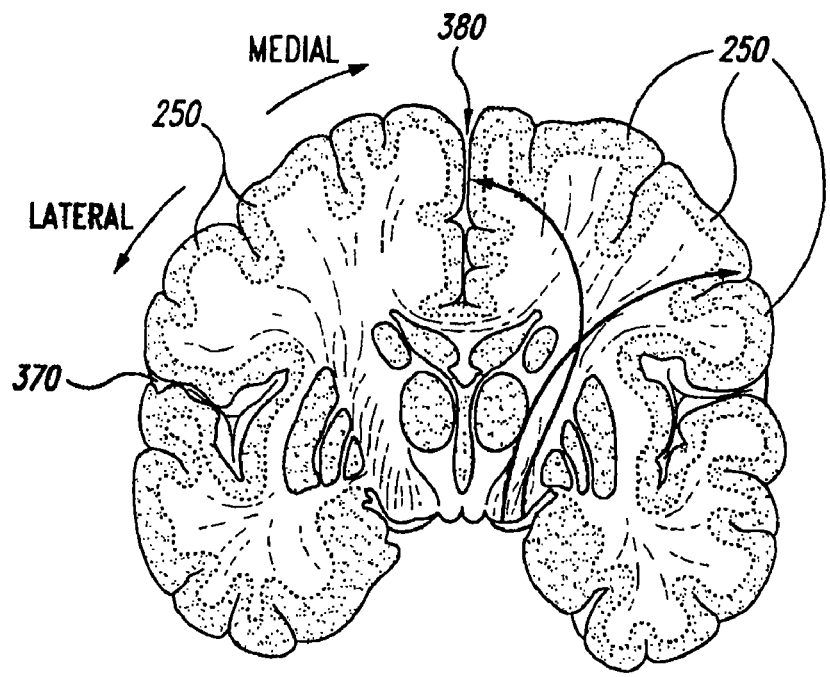
FIG. 3C is a lateral cross-sectional view of the cortex of a patient showing additional stimulation sites in accordance with additional embodiments of the invention.

FIGS. 3A-3C illustrate several embodiments of the implanting procedure 108 for implanting electrodes at a stimulation site. FIG. 3A, more specifically, is a schematic side view of the brain 200 illustrating one embodiment of implanting a linear electrode array 310 at a stimulation site 300a proximate to the dura and over the precentral gyrus 250. In this embodiment, the linear electrode array 310 has a plurality of electrodes 320 arranged along a single row, but in other embodiments the linear electrode array 310 may have only one electrode 320. For example, the electrode array 310 can have only a single electrode 320 (i.e., a contact) instead of an array of electrodes. The electrodes 320 can be circular contacts each having a surface area of approximately 5 mm² and being spaced apart by about 7.5 mm. In other embodiments, the electrodes can be other shapes and have other configurations, such as an elongated electrode. The linear electrode array 310 has a lead 322 coupled to the electrodes 320 and an implanted pulse generator implanted above the neck or at a subclavicular location. The lead 322 is tunneled through the patient using standard techniques.

The linear electrode array 310 can be positioned so that the row of electrodes 320 extends in a medial to lateral direction generally parallel with the central sulcus 244. The electrodes 320 are also superimposed over the precentral gyrus 250. The linear electrode array 310 generally has a plurality of electrodes 320 to provide extensive coverage over the precentral gyrus 250 and thus activate a large number of neurons in the motor cortex (e.g., use all of the electrodes) or only discrete populations of neurons in the motor cortex with only a single implantation of an electrode array (e.g., activate only selected electrodes). The electrode array 310 can be implanted so that the electrodes are proximate to the dura such as at an epidural or subdural location.

FIG. 3B is a side-view of the brain 200 illustrating another embodiment for implanting an electrode array proximate to the dura at the stimulation site. In this embodiment, the stimulation site 300b is located over the precentral gyrus 250 and the postcentral gyrus 260. A grid electrode array 330 is implanted at the stimulation site 300b proximate to the dura. The grid electrode array 330 can include a plurality of first electrodes 340a arranged along a first row and a plurality of second electrodes 340b arranged along a second row. The first and second rows of electrodes 340a-b can extend generally at an oblique angle relative to the central sulcus 244. The grid electrode array 330 also has a lead 342 coupled to the electrodes 340a-b and an implanted pulse generator. As with the linear electrode array 310, the grid electrode array 330 can be implanted so that the electrodes are proximate to the dura.

One aspect of several embodiments of the invention is that the stimulation sites 300a and 300b shown on FIGS. 3A and 3B are located relative to the precentral gyrus, the central sulcus 244, and/or the postcentral gyrus 260 using the imaging and site selection procedures 102-104 described above with respect to FIGS. 2A and 2B. This enables the stimulation to be applied to desired locations on the cortex with much greater accuracy than previous methods that rely solely on the external anatomical features of the patient. The greater precision of locating the stimulation sites 300a-b for implanting the electrode arrays is expected to significantly enhance the efficacy of stimulation treatments for treating PD and other movement disorders.

Another aspect of several embodiments is that the efficacy of the stimulation treatment can also be enhanced by locating the stimulation sites 300a-b at a desired superior-inferior location along the precentral gyrus and/or the postcentral gyrus relative to the sylvian fissure and the interhemispherical fissure. FIG. 3C, for example, is a lateral section view taken along line 3C-3C of FIG. 3B. The stimulation site can be located more towards the sylvian fissure 370 for treating predominant symptoms of speech disorders or towards the interhemispherical fissure 380 for treating predominant symptoms of gait disorders. The superior-inferior location along the precentral gyrus 250 and/or the postcentral gyrus 260 can accordingly be predicated by the symptomotology of the function that is affected by the movement disorder.

Figure 4:
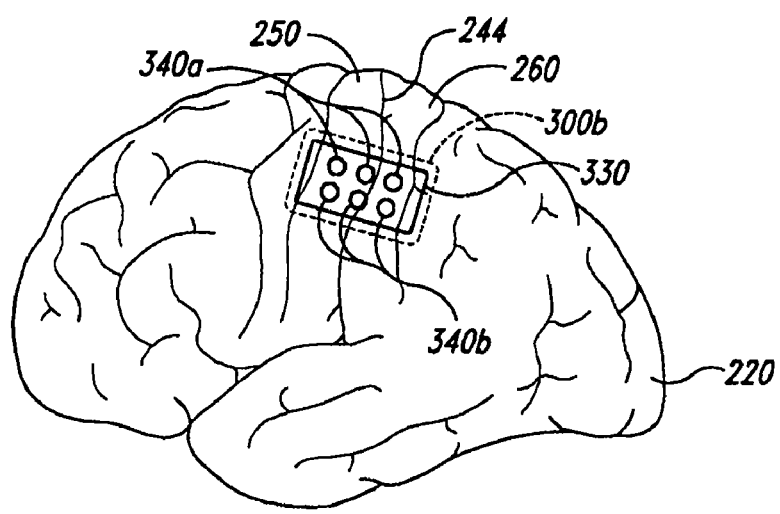
FIG. 4 is a side view of a brain of a patient showing one embodiment of applying neural stimulation to treat movement disorders.

FIG. 4 is a side view illustrating several embodiments of applying neural stimulation directly to the stimulation site. More specifically, FIG. 4 illustrates the grid electrode array 330 positioned at the stimulation site 300b over the precentral gyrus 250, the central sulcus 244, and the postcentral gyrus 260. The neural stimulation can comprise passing an electrical current through the electrodes 340a-b to the stimulation site 300b. In one embodiment, the electrical current can be applied to a single one of the electrodes 340a or 340b to provide a monopolar pulse of current to a small area of the cortex 220. A return electrode can be positioned elsewhere in the patient, such as on the other side of the patient's brain or at a subclavicular location. The return electrode can be a portion of a pulse generator or another electrode implanted elsewhere in the patient. In other embodiments, electrical current can be passed through all of the electrodes 340a-b or only a subset of these electrodes to activate larger or different populations of neurons. In these embodiments, the potential applied to the electrodes 340a-b can be the same across all of the activated electrodes to provide monopolar stimulation at the stimulation site. This embodiment also typically has a return electrode implanted elsewhere in the patient as explained above. In other embodiments, some of the electrodes can be biased with a positive polarity and other electrodes can be biased with a negative polarity. For example, the first electrodes 340a can be biased with one polarity and the second electrodes 340b can be biased with an opposite polarity. This embodiment provides a bipolar stimulation to the cortex 220. The particular configuration of the electrodes can be optimized after implantation to provide the most efficacious therapy for the patient.

The particular waveform of the stimuli depends upon the symptoms of the particular patients. In one embodiment, the stimulus can have a waveform with a current of approximately 0.5 mA to 10 mA, a pulse duration of approximately 20 microseconds-500 milliseconds, and a frequency of approximately 10 Hz-200 Hz. In other embodiments, the electrical stimulus can have a current of approximately 3 mA to 8 mA, a pulse duration of 100 microseconds-200 microseconds, and a frequency of approximately 20 Hz-50 Hz. In still other embodiments, the current can be approximately 4 mA to 6 mA, and more particularly approximately around 5 mA. The waveforms of any of the foregoing embodiments can have a voltage of approximately: 0.25 V to 5.0 V in many applications; 0.5 V to 3.5 V in more specific applications; 2.0 V to 3.5 V in still more specific applications; and 3.0 V in a particular application. Additionally, the pulse duration can be in the range of 90-180 microseconds. The stimulus can be applied for a period of 0.5 hour-4.0 hours, and in many applications the therapy is applied for a period of approximately 0.5 hour-1.5 hours. In other embodiments, the stimulation can be applied continuously, or only during waking periods but not sleeping periods. Examples of specific stimulation protocols for use with an electrode array at an epidural stimulation site over the precentral gyrus are as follows:

EXAMPLE 1

An electrical stimulus having a current of approximately 0.1 mA to 10 mA, an impedance of 600 to 1000 Ohms, a pulse duration of 160 microseconds, and a frequency of approximately 130 Hz. The therapy is not applied continuously, but rather during 30-60 minute intervals.

EXAMPLE 2

The stimulus has a current of approximately 0.1 mA to 10 mA, a pulse duration of approximately 150-180 microseconds, and a frequency of approximately 25 Hz-31 Hz. The stimulus is applied continuously during waking periods, but it is discontinued during sleeping periods to conserve battery life of the implanted pulse generator.

EXAMPLE 3

The stimulus has a current of approximately 2 mA to 4 mA, a pulse duration of approximately 90 microseconds, and a frequency of approximately 30 Hz. This stimulus is applied continuously during waking and sleeping periods, but it can be discontinued during sleeping periods.

Figure 5:
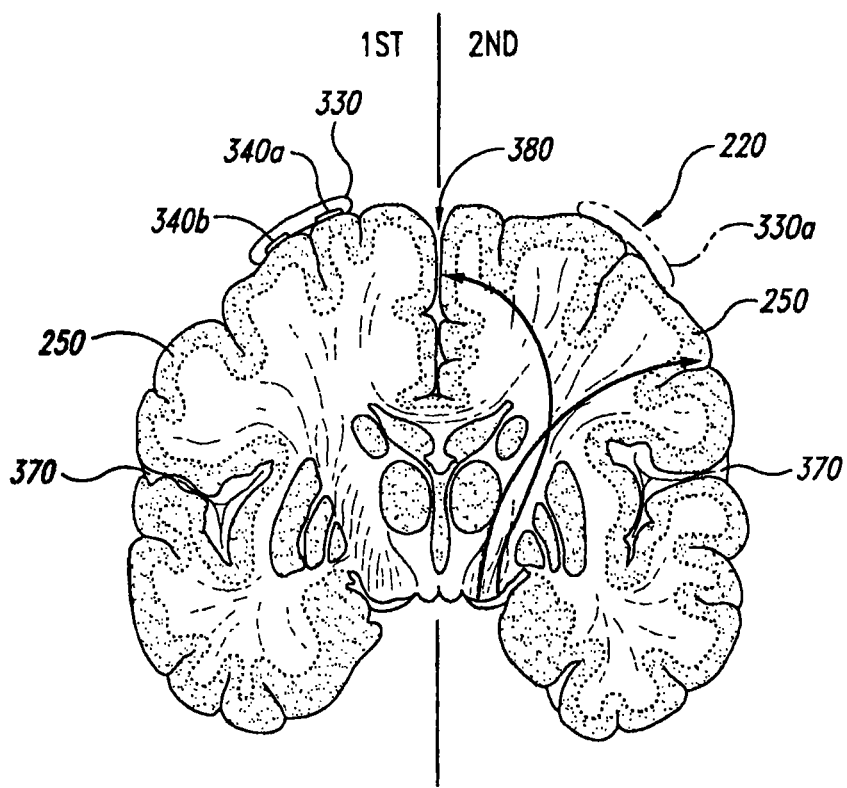
FIG. 5 is a cross-sectional view of the cerebral cortex of a patient illustrating another embodiment of treating movement disorders in accordance with the invention.

FIG. 5 illustrates another aspect of an embodiment of the invention. In many cases of PD, the symptoms are manifested to a greater extent on one side of the body than the other. For example, a patient may have a tremor in both hands, but usually one hand will have a tremor worse than the other hand. In this embodiment, the patient's body is divided into a first side and a second side opposite the first side relative to a medial axis (e.g., right side-left side), and only one side of the cortex is stimulated to treat the disorder on both sides of the body. This embodiment can be carried out by implanting the electrode array 320 or 330 at a stimulation site on only the first side of the patient when the disorder of a motor function is greater on the second side of the patient. For example, this embodiment can also include implanting one or more electrodes at a homologous location on the contralateral hemisphere relative to the movement disorder. The single electrode array can provide a bilateral affect that not only treats the disorder associated with the second side of the patient, but also treats the disorder associated with the first side of the patient. For example, if the patient experiences a bilateral tremor that is worse on the right side compared to the left side, then an electrode array can be implanted proximate to the dura over only the left hemisphere of the cortex 220. The bilateral effect of the single-side stimulation may be enhanced using monopolar stimulation techniques in which the electrodes are biased with the same polarity. The bilateral effect may be caused by activation of commissural neurons (large pyramidal cells) in the deep portion of layer III of the motor cortex. Subsequent to activation, these neurons can depolarize complimentary cell groups in the contralateral hemisphere via the corpus callosum.

In a specific embodiment, by accurately locating the electrodes over the precentral gyrus using the imaging and site selection procedures 102 and 104 described above, the electrode may maximally effect the contralateral lower extremity musculature and also the ipsilateral muscle groups. It is expected that the placement should be sufficiently remote from the interhemispheric fissure to avoid venous damage or occlusion. As a result, the single-side stimulation site may be particularly advantageous in certain situations because it requires only a single electrode array to be planted relative to a single hemisphere of the cortex 220 of the patient. This reduces the invasiveness and the risk associated with surgery.

FIG. 5 also illustrates another embodiment in which an electrode array 330a (shown in broken line) is implanted at a site on the ipsilateral hemisphere of the brain relative to the side of the body most affected by the movement disorder. The electrode array 330a can be implanted by itself such that it is the only electrode array. In a different embodiment, however, both of the electrode arrays 330 and 330a can be implanted at homologous and/or non-homologous regions relative to the movement disorders on both hemispheres of the brain. Additionally, the electrode array 330a can have only a single electrode as described above with respect to the electrode array 330.

Figure 6:
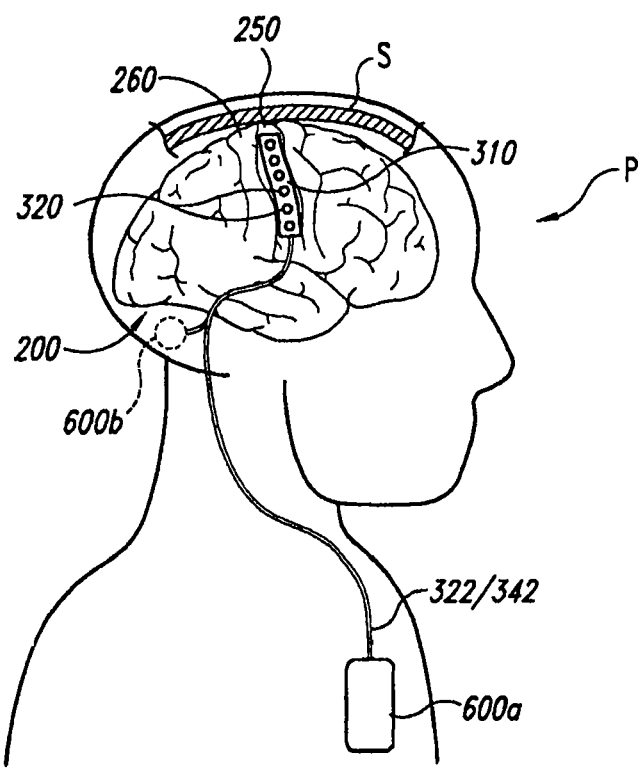
FIG. 6 is a schematic view illustrating a system for treating movement disorders in accordance with the invention.

FIG. 6 is a schematic view illustrating embodiments of systems for treating movement disorders in accordance with the invention. The system can include the linear electrode array 310 coupled to an implanted pulse generator 600a implanted at a subclavicular location in the patient P. The grid electrode array 330 can be substituted for the linear electrode array 310. In either of these embodiments, a lead 322/342 is tunneled between the implanted pulse generator 600a and the electrode array. In another embodiment, the system has an implanted above-neck pulse generator 600b that is smaller and configured to be implanted at a location above the neck of the patient P. The above-neck implanted pulse generator 600b can be planted posteriorly of the ear of the patient P. In each of these embodiments, the electrode arrays 310 or 330 (not shown in FIG. 6) are implanted underneath the scull S of the patient P at an epidural or subdural stimulation site as set forth above.

B. Embodiment for Treating Movement Disorders

Figure 7:
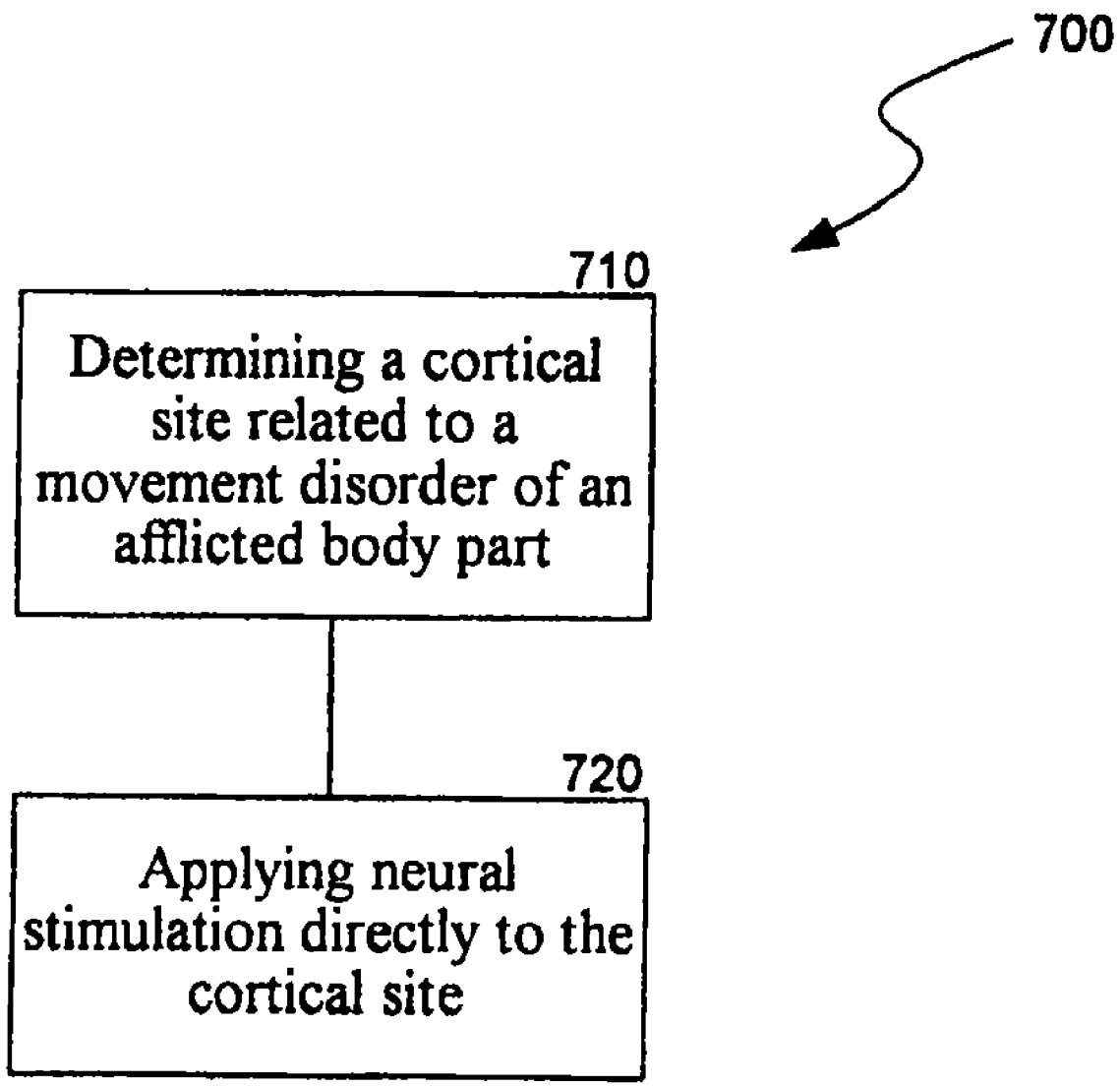
FIGS. 7-9 are flow charts of methods in accordance with embodiments of the invention for treating movement disorders.

FIG. 7 is a flow chart illustrating additional methods for treating movement disorders in accordance with additional embodiments of the invention. In one embodiment, a method 700 includes a site selection procedure 710 including determining a cortical site related to a movement disorder of an afflicted body part of the patient. In one embodiment, the site selection procedure 710 includes obtaining a representation of neural activity occurring in the cortex of the patient, and correlating an area of neural activity with the afflicted body part. In a related embodiment, the site selection procedure 710 can include providing a representation of neural activity in the cortex of the brain of a patient, identifying a neural activation area on the representation considered to be related to a body part of the patient affected by a movement disorder, and selecting the cortical site on the patient by referencing the identified neural activation area to the anatomy of the patient.

In patients having little or no tremor symptoms, a representation of neural activity occurring in the cortex can be obtained or provided by imaging neural activity in the cortex using a neural imaging technique while performing a task related to the affected body part. For example, the representation of neural activity in the cortex can be obtained by imaging cortical neural activity while (a) the patient mentally concentrates on moving the affected body part, (b) the affected body part is moved by the patient, (c) an electrical pulse is applied to the affected body part, and/or (d) another person or device passively moves the affected body part. In other embodiments, obtaining a representation of neural activity in the brain can include collecting data of neural activity in the cortex of the patient related to the affected body part without necessarily generating an image. The collected data can be stored in a memory and processed to generate anatomical coordinates and/or an image of the neural activity.

The site selection procedure 710 is expected to increase the efficacy of the stimulation therapy and provide additional benefits. For example, having the patient concentrate on moving the affected body part or actually move the affected body part while imaging the neural activity in the cortex is expected to provide an accurate indication of the area(s) in the cortex where neural activity for controlling the motor function of the affected body part is performed. Similarly, applying an electrical pulse to the affected body part while imaging neural activity in the cortex is expected to provide another accurate indication of where neural activity occurs for controlling the motor function of the affected body part. By providing an accurate indication of the location of neural activity related to the affected body part, the method 700 is expected to operate at low electrical potentials to reduce unwanted collateral stimulation of neurons and prolong the battery life of an implanted pulse generator. Moreover, such precise location of the electrodes enhances the efficacy of the stimulation procedure because the neurons that are involved in controlling the affected body part are more likely to be stimulated in a controlled manner.

The method 700 further includes a stimulation procedure 720 that involves applying neural stimulation directly to the cortical site. The stimulation procedure can be preceded by implanting an electrode unit proximate to the dura mater at the cortical site. The electrode unit can have a single electrode or an array with a plurality of electrodes as explained above. The stimulation procedure 720 can include any of the electrical waveforms set forth above. In additional embodiments, the stimulation procedure can include applying an electrical waveform having a frequency of approximately 5-1000 Hz. In more specific embodiments, the stimulation procedure 720 can include applying an electrical waveform having a frequency of approximately 10-60 Hz, and more specifically at a frequency of 20 Hz or 50 Hz. Other examples could be at higher frequencies of 90-150 Hz or in a narrower range of 100-120 Hz.

Figure 8:
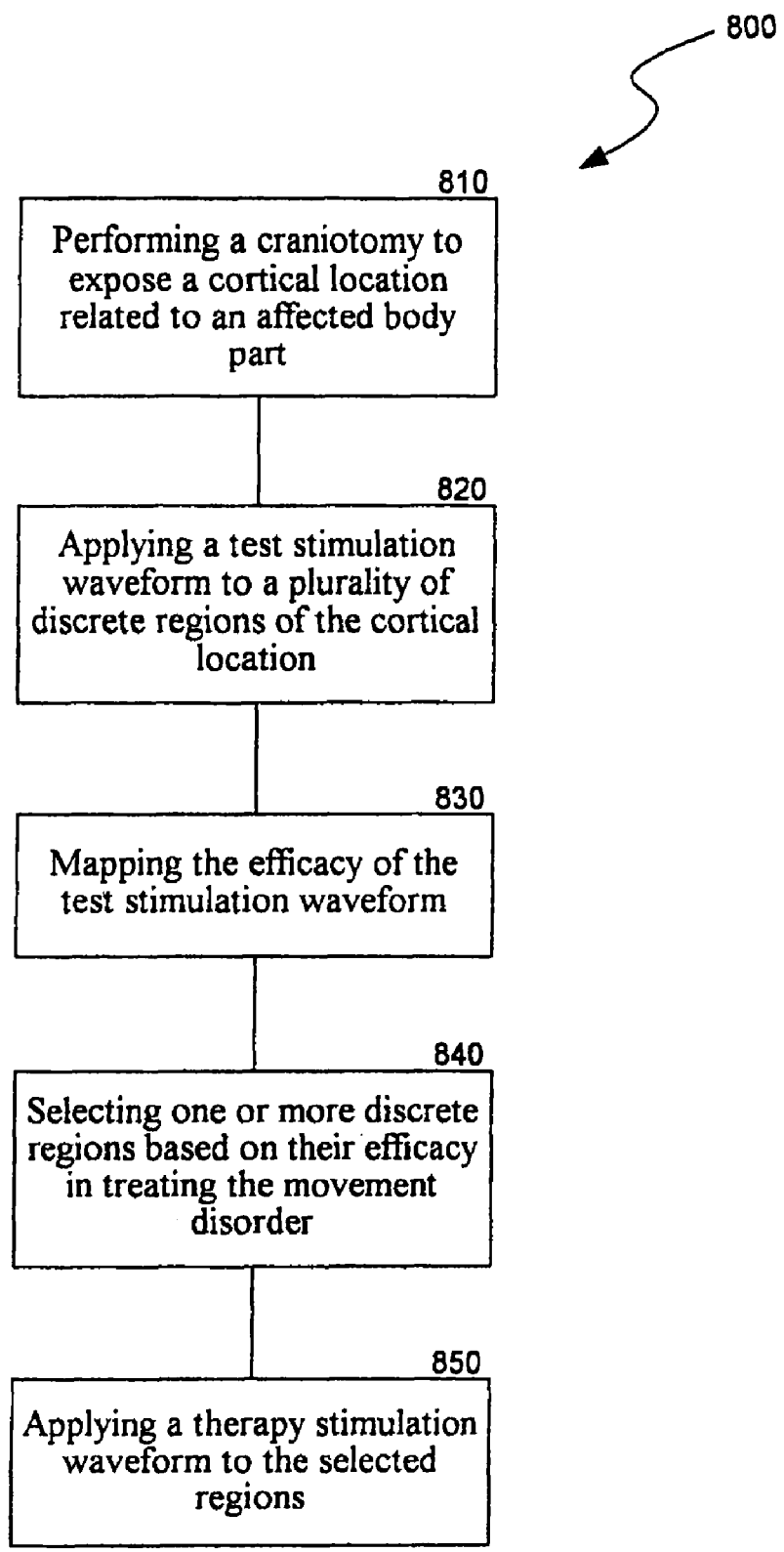

FIG. 8 is a flow chart illustrating another method for treating movement disorders in accordance with additional embodiments of the invention. In one embodiment, the method 800 includes performing a craniotomy 810 to expose a cortical location related to an affected body part. The craniotomy 810 can expose subdural or epidural tissue. The method 800 further includes a test procedure 820 and a mapping procedure 830. The test procedure 820 includes applying a test stimulation waveform to a plurality of discrete regions of the cortical location. In one embodiment of the test procedure 820, a single electrode is moved to different discrete locations of the cortical region exposed by the craniotomy and an electrical pulse is applied to each location separately. In other embodiments, the test procedure 820 includes implanting an electrode array having a plurality of electrodes such that each electrode is adjacent to a discrete region of the cortical location. This embodiment includes applying the test stimulation waveform separately to one or more of the individual electrodes in different combinations. Both of these embodiments of the test procedure 820 apply the test stimulation waveform to the discrete regions of the cortical location at separate time periods. The mapping procedure 830 includes (a) verifying the proper electrode location and/or (b) measuring the efficacy of the test stimulation waveforms as they are applied to the different discrete regions of the cortical location. The mapping procedure can occur while the patient is under an anesthetic, and it can also apply electrical pulses at a current that is sufficient to provoke a response. After verifying the electrode location during surgery, the mapping procedure 830 can further include monitoring the decrease and/or increase in the tremor of a body part affected by PD as the test waveform is applied to the different discrete regions. The method 800 further includes a selection procedure 840 in which one or more of the discrete regions is selected based upon the efficacy of the discrete regions for treating the movement disorder. The selection procedure 840 accordingly determines which electrode(s) receive electrical pulses for treating the movement disorder. The method 800, accordingly, further includes a stimulation procedure 850 including applying a therapy stimulation waveform to the selected regions of the cortical location.

Figure 9:
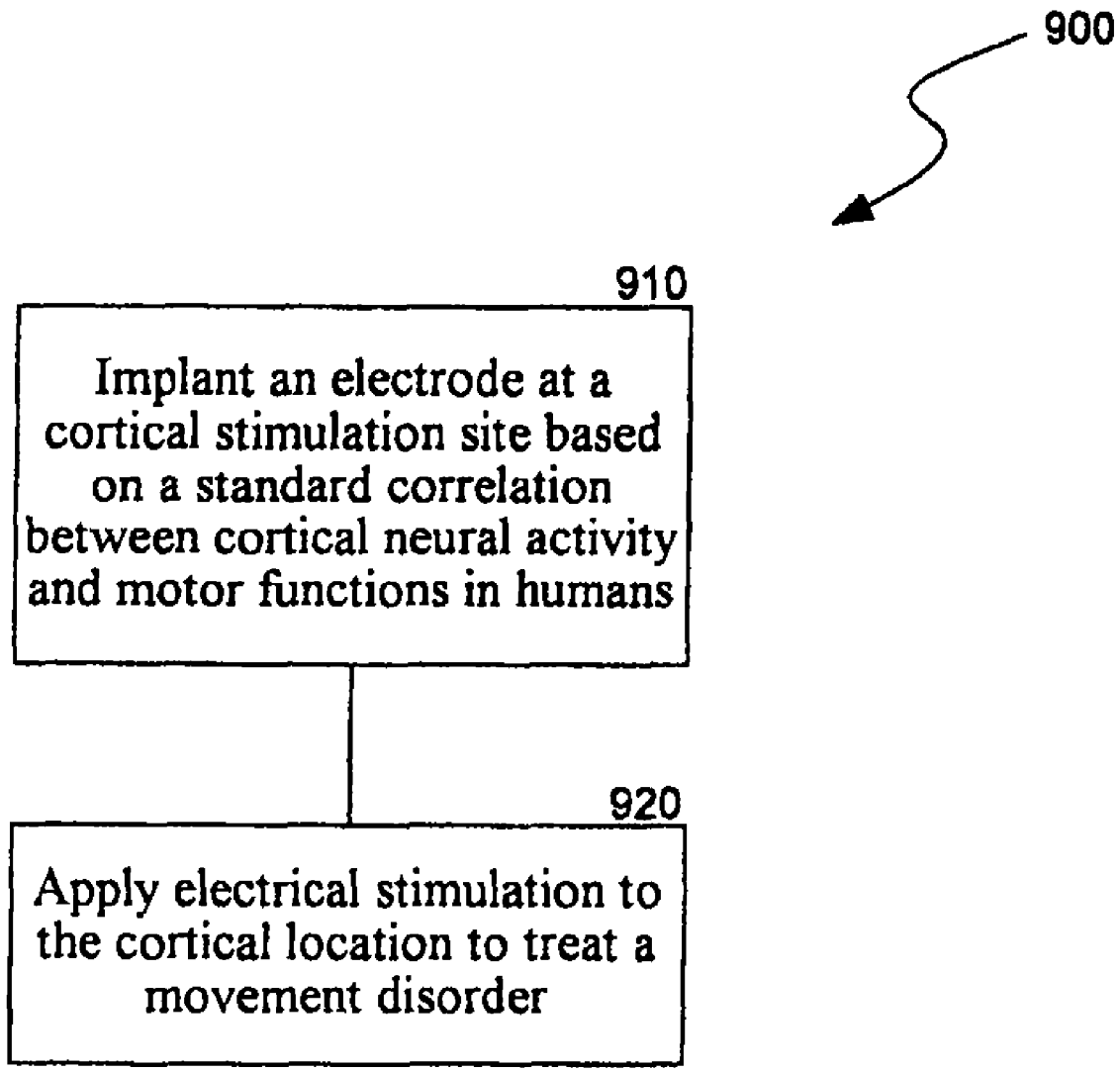

FIG. 9 is a flow chart of another method 900 for treating movement disorders in accordance with another embodiment of the invention. The method 900 includes an implanting procedure 910 in which an electrode is implanted at a cortical stimulation site based upon a standard correlation between cortical neural activity and motor functions in humans. For example, an electrode array can be implanted at a cortical stimulation site based upon the standard correlation between cortical neural activity and motor functions in humans, and in particular the standard location for neural activity in humans for motor control of the affected body part. The implanting procedure 910 accordingly does not necessarily need to select the stimulation site based upon an image, data or other information to obtain or provide a representation of neural activity in the brain related to the affected body part. The method 900 further includes a stimulation procedure 920 involving applying electrical stimulation to the cortical location to treat a movement disorder.

From the foregoing, it will be appreciated that specific embodiments of the invention have been described herein for purposes of illustration, but that various modifications may be made without deviating from the spirit and scope of the invention. For example, the leads of the electrode arrays may be coupled to an external pulse generator instead of an implanted pulse generator. In an alternate embodiment, the stimulation site can be selected at an area of the cortex that is not normally associated with the function of the body part(s) affected by the movement disorder (e.g., non-homologous regions). This embodiment accordingly places the electrodes at other neurofunctional areas that control other movement and/or speech functions. In still other embodiments, electrode arrays having different configurations of electrodes can be implanted on opposing hemispheres of the cortex. Furthermore, in an additional embodiment, transcutaneous magnetic stimulation can be applied to the selected stimulation site before implanting the electrodes to estimate the response and refine the location of the stimulation site. For example, a stimulation site can be selected using an imaging modality (e.g., MRI, fMFI, etc.) and/or externally estimating the site according to the normal location for neural activity associated with the movement disorder, and then transcutaneous magnetic stimulation can be applied at the stimulation site and/or neighboring areas before implanting the electrode. The precise location for the stimulation site can then be modified according to the results of the transcutaneous magnetic stimulation in a manner similar to the mapping procedure 830 described above. Accordingly, the invention is not limited except as by the appended claims.

We claim:

1. A method for treating movement disorders, comprising:
   selecting a stimulation site at least proximate to the dura and along the precentral gyrus of a patient by imaging at least one of the precentral gyrus, central sulcus and/or postcentral gyrus of the patient relative to an external marker on the patient and using symptomatology of the function that is affected by the movement disorder to determine the superior-inferior location along the precentral gyrus; and
   applying neural stimulation directly to the stimulation site.

2. The method of claim 1, further comprising implanting an electrode at the stimulation site, and wherein applying neural stimulation comprises passing an electrical current through the electrode.

3. The method of claim 2 wherein implanting the electrode comprises positioning an array having a plurality of electrodes over only the precentral gyrus of the patient.

4. The method of claim 2 wherein implanting the electrode comprises positioning an array having a plurality of electrodes such that at least one electrode is over the precentral gyrus and at least one other electrode is over the postcentral gyrus of the patient.

5. The method of claim 1, further comprising implanting an electrode array having a plurality of first electrodes arranged in a first row and a plurality of second electrodes arranged in a second row at the stimulation site, and wherein applying neural stimulation comprises passing an electrical current through at least one of the electrodes.

6. The method of claim 5 wherein implanting the electrode array comprises positioning the first and second rows at an oblique angle relative to the central sulcus.

7. The method of claim 5 wherein implanting the electrode array comprises positioning one of the first electrodes and one of the second electrodes over the precentral gyrus of the patient, and positioning another one of the first electrodes and another one of the second electrodes over the postcentral gyrus of the patient.

8. The method of claim 1 wherein applying neural stimulation directly to the stimulation site comprises delivering an electrical current directly to the dura of the patient at the stimulation site.

9. The method of claim 1 wherein applying neural stimulation directly to the stimulation site comprises delivering an electrical current directly to the patient at least proximate to the dura over the stimulation site.

10. The method of claim 9 wherein delivering an electrical current directly to the patient comprises applying a unipolar electrical potential to an electrode implanted at the stimulation site.

11. The method of claim 9 wherein delivering an electrical current directly to the patient comprises applying a unipolar electrical potential to a plurality of electrodes implanted at the stimulation site.

12. The method of claim 9 wherein delivering an electrical current directly to the patient comprises applying a bipolar electrical potential to a plurality of electrodes implanted at the stimulation site.

13. The method of claim 1 wherein the patient has a movement disorder that is worse on a first side of the patient than on a second side of the patient opposite the first side, and wherein the method further comprises implanting an electrode over the precentral gyrus on the second side of the patient only.

14. The method of claim 1 wherein the function that is affected by the movement disorder is gait and the superior-inferior location along the precentral gyrus comprises a location closer to the interhemispheric fissure than the Sylvian fissure.

15. The method of claim 1 wherein the function that is affected by the movement disorder is speech and the superior-inferior location along the precentral gyrus comprises a location closer to the Sylvian fissure than the interhemispheric fissure.

16. The method of claim 1 wherein the movement disorder is Parkinson's Disease.

* * * * *